United States Patent [19]

Dickinson et al.

[11] 4,182,666

[45] Jan. 8, 1980

[54] OXYGEN SENSORS

[75] Inventors: Thomas Dickinson, Newcastle-upon-Tyne; John V. Dobson, Hartlepool, both of England

[73] Assignee: National Research Development Corporation, London, England

[21] Appl. No.: 886,115

[22] Filed: Mar. 13, 1978

[30] Foreign Application Priority Data

Mar. 15, 1977 [GB] United Kingdom ............... 10840/77

[51] Int. Cl.² ..................... G01N 27/30; G01N 27/46
[52] U.S. Cl. ................................................. 204/195 P
[58] Field of Search ............... 204/195 P, 1 P; 324/29

[56] References Cited

U.S. PATENT DOCUMENTS

| | | | |
|---|---|---|---|
| 3,689,394 | 9/1972 | Davies et al. | 204/195 P |
| 3,882,012 | 5/1975 | Dickinson et al. | 204/195 P |

*Primary Examiner*—G. L. Kaplan

*Attorney, Agent, or Firm*—Stevens, Davis, Miller & Mosher

[57] ABSTRACT

An oxygen sensor is described which includes an electrochemical cell having a gas diffusion electrode which includes a porous metal layer and another layer substantially non-porous to the electrolyte but porous to oxygen, interposed between the porous metal layer and the environment of the sensor as the cathode or working electrode, a salt electrolyte capable of being molten at the temperature of operation of the sensor, a counter electrode as anode, a reference electrode, means for maintaining the working electrode at a constant potential with reference to the reference electrode, and means for determining the current flowing in the cell due to the reduction of oxygen present in the environment of the cell at the gas diffusion electrode and characteristic of the amount of oxygen present, the oxygen sensor including a noble metal and noble metal/noble metal oxide electrode as the counter electrode and the reference electrode respectively. Platinum is the preferred noble metal.

7 Claims, 4 Drawing Figures

OXYGEN SENSORS

The present invention relates to improvements in oxygen sensors of the type disclosed and claimed in U.K. Pat. Specification No. 1,318,189 in which the working or oxygen diffusion electrode is maintained at a constant potential with reference to a reference electrode.

In the following specification reference to an oxygen sensor of the type described means an oxygen sensor including an electrochemical cell having a gas diffusion electrode as the cathode or working electrode, a salt electrolyte capable of being molten at the temperature of operation of the sensor, a counter electrode as anode, a reference electrode, and means for maintaining the working electrode at a constant potential with reference to the reference electrode; the gas diffusion electrode including a porous metal layer and another layer substantially non-porous to the electrolyte but porous to oxygen, interposed between the porous metal layer and the environment of the sensor.

U.K. Pat. Specification No. 1,318,189 discloses counter electrodes which are metal/metal oxide systems in which the metal is any metal stable in contact with the molten salt electrolyte and capable of forming an oxide substantially insoluble in said molten salt electrolyte. Suitable metals disclosed include tin, zinc and alloys thereof.

In accordance with the present invention an oxygen sensor of the type described includes a noble metal as the counter electrode and a noble metal/noble metal oxide electrode as the reference electrode. In this specification the term "noble metal" is used to mean metals having a relatively positive electrode potential, and which do not readily enter into chemical combination, for example gold, silver and platinum.

Advantageously the noble metal is platinum and in a preferred embodiment of the present invention an oxygen sensor of the type described includes a silver metallised polytetrafluoroethylene membrane as the oxygen diffusion electrode, a platinum/platinum oxide electrode as the reference electrode and platinum as the counter electrode.

The use of the noble metal/noble metal oxide electrode as a reference electrode in this system is surprising and it is believed that the method of preparation of the electrode is important to this result. For example a suitable platinum/platinum oxide reference electrode may be prepared by thoroughly cleaning platinum wire by boiling in aqua regia followed by immersion in molten potassium nitrate at a temperature in excess of 400° C. for at least one hour while bubbles of gas evolve from around the wire.

Preferably the oxygen diffusion electrode is a film of polytetrafluoroethylene 6 $\mu$m thick one side of which has been covered with a coating of evaporated or sputtered gold followed by one of silver to ensure good adhesion between the silver and the polytetrafluoroethylene.

The salt electrolyte is preferably an alkali metal nitrate eutectic mixture and excellent results have been obtained using the eutectic of sodium, potassium and lithium nitrates having substantially the composition $NaNO_3$—30 moles %, $KNO_3$—53.5 moles % and $LiNO_3$—16.5 moles %.

It is an advantage of oxygen sensors employing molten salt electrolytes that they are capable of operating at temperatures in excess of the boiling point of water but they have the potential disadvantage of being unable to operate at a temperature below the solidification temperature of the electrolyte. In accordance with an aspect of the present invention an oxygen sensor of the type described includes a heater and a thermostatic device which are arranged to co-operate so that the sensor may be used in environments having a temperature below the melting point of its molten salt electrolyte. A heating coil may be provided external to the electrochemical cell of the sensor, or a heating coil may be provided in the electrolyte, or both.

The invention will now be described by way of example only with reference to the accompanying drawings of which:

Figure 1:
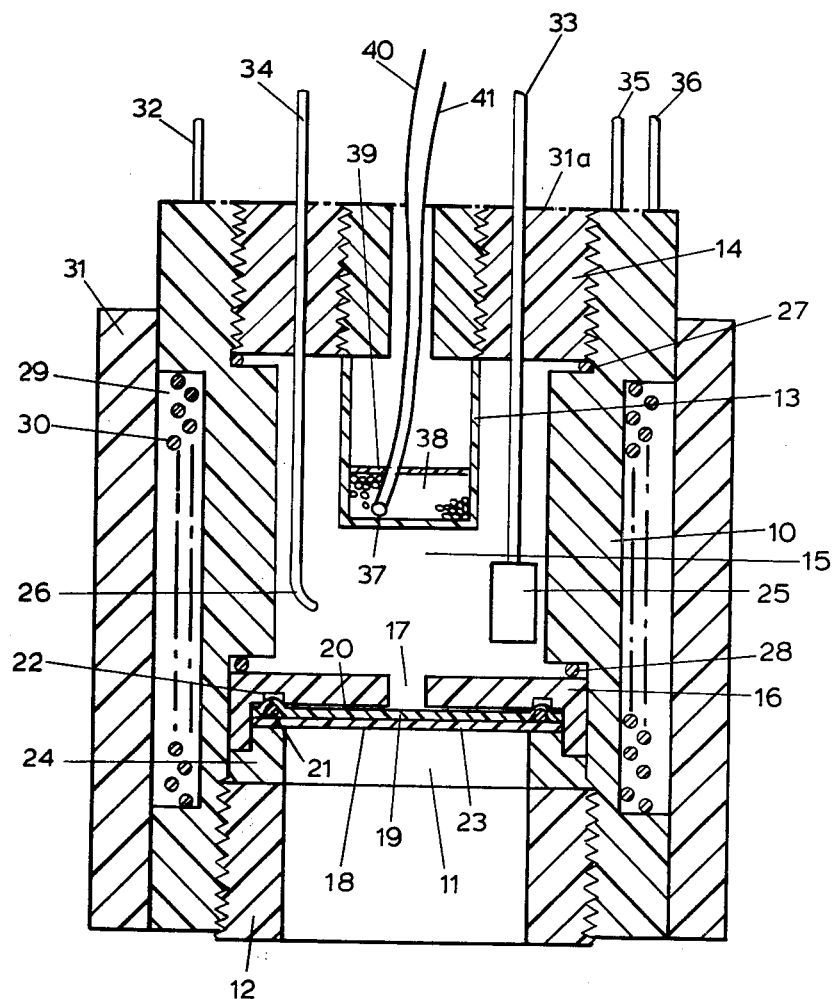
FIG. 1 is a cross sectional view of an oxygen sensor cell in accordance with the present invention.

Referring now to FIG. 1 the sensor is constructed from polytetrafluoroethylene and consists of an annular body 10 within which an oxygen diffusion electrode assembly 11 is held in position by an externally threaded annular plug 12 and a deformable thin walled bag 13 is held by externally threaded plug 14. The oxygen diffusion electrode assembly 11, the annular body 10, and the deformable bag 13 define an electrode cavity 15 within the sensor.

The oxygen diffusion electrode assembly 11 consists of a mount 16 having a hole 17 communicating with the electrode cavity 15. The mount 16 has a recess 18 in which is mounted a 6 $\mu$m polytetrafluoroethylene film 19 having a coating of evaporated gold and one of silver 20 on the side toward the hole 17 in the mount 16. An O-ring seal 21 co-operating with a ring groove 22 in the mount 16 holds the coated polytetrafluoroethylene membrane 19/20 in position, a porous polytetrafluoroethylene sheet 23 being provided and the whole being held in position by an annular plug 24 and the externally threaded plug 12.

The deformable bag 13 is carried in the externally threaded plug 14 which carries a platinum foil 25 on a platinum wire as counter electrode (anode) and a platinum/platinum oxide electrode 26 as reference electrode. O-rings 27 and 28 seal the electrolyte cavity 15 at the top and bottom respectively.

The body 10 of the sensor has a circumferential recess 29, which contains winding of heating wire 30 and a sleeve 31 is provided to enclose the body 10.

The sensor has a conventional electrical connector (not shown) at the end remote from the oxygen diffusion electrode 11. The interface between the electrical connector and the sensor is illustrated schematically by the chain dotted line 31a. The electrical leads are also illustrated schematically and they are; to the oxygen diffusion electrode, ie the coated polytetrafluoroethylene membrane 19/20 (reference 32), to the platinum counter electrode 25 (reference 33), to the platinum/platinum oxide reference electrode 26 (reference 34), and to the heating wire 30 (references 35 & 36).

The sensor is also provided with a thermocouple 37 immersed in lead shot 38 to facilitate the taking of the temperature of the cell. A membrane 39 is provided to retain the lead shot in position. The thermocouple 37 has leads 40 and 41 by which the temperature of the sensor may be monitored in order to control the application of heat by the heating wire 30 so that the sensor may be maintained at a desired operating temperature.

The deformable bag 13 communicates with the atmosphere and is provided in order to equalize pressure differences between the cell interior and the atmosphere in which the cell is operating. This is to avoid rupture of the membrane 19/20.

The platinum/platinum oxide electrode 26 is prepared by coating a platinum wire in a bath of molten potassium nitrate. The tip (about 0.5 cm) of a length of platinum wire is cleaned by boiling in aqua regia for a few minutes, followed by washing and drying. It is then immersed in molten potassium nitrate at a temperature in excess of 400° C. for at least one hour. The best type of electrode is obtained when gas bubbles are evolved from the surface of the platinum wire. The electrode is then washed and carefully dried, care being taken to ensure that it is not handled.

The electrolyte is the eutectic of sodium, potassium, and lithium nitrates have the composition sodium nitrate—30 moles %, potassium nitrate—53.5 moles %, and lithium nitrate—16.5 moles %.

The gas diffusion electrode is assembled as follows. The molten eutectic as defined above is cast into as thin a film as possible. Either by use of a shallow dish or by running the molten mixture down a sloping glass plate. A disc of eutectic is cut having diameter about the same as the internal diameter of the O-ring 21. The interior of the recess 18 of the mount 16 is coated with electrically conducting araldite and the disc of eutectic placed in position within the space bounded by the circular groove 22.

The metallised membrane 19/20 is placed over the eutectic disc with the metal surface 20 towards the disc and the O-ring 21 gently pushed into the circular groove 22. The sheet of porous polytetrafluoroethylene 23 is placed over the O-ring 21 and the annular plug 24 pressed into position to ensure that the O-ring 21 is firmly seated in the circular groove 22. The gas diffusion electrode assembly 11 is then placed in the body 10 and held there by the externally threaded annular plug 12, the whole heated to a temperature of 150° C. and filled with molten eutectic. The partially assembled sensor is left thus for 2 hours, during which time it is periodically tapped to ensure that all gas bubbles are removed. The central deformable bag 13 carried in the externally threaded plug 14 is heated at 150° C. for the same time and then slowly screwed into place. An overflow hole (not shown in the drawing) is provided through which excess eutectic is removed. Once the externally threaded plug 14 has been fully screwed home the sensor is allowed to cool and the overflow hole sealed with silicone rubber. The heating coil, thermostat, sleeve and electrical connectors are then assembled in known manner. The cell may also be provided with a polytetrafluoroethylene covered heating coil immersed in the electrolyte.

Conveniently the parts of the sensor are in PTFE but any material resistant to the electrolyte and capable of resisting the operating temperature of the device may be used.

Figure 2:
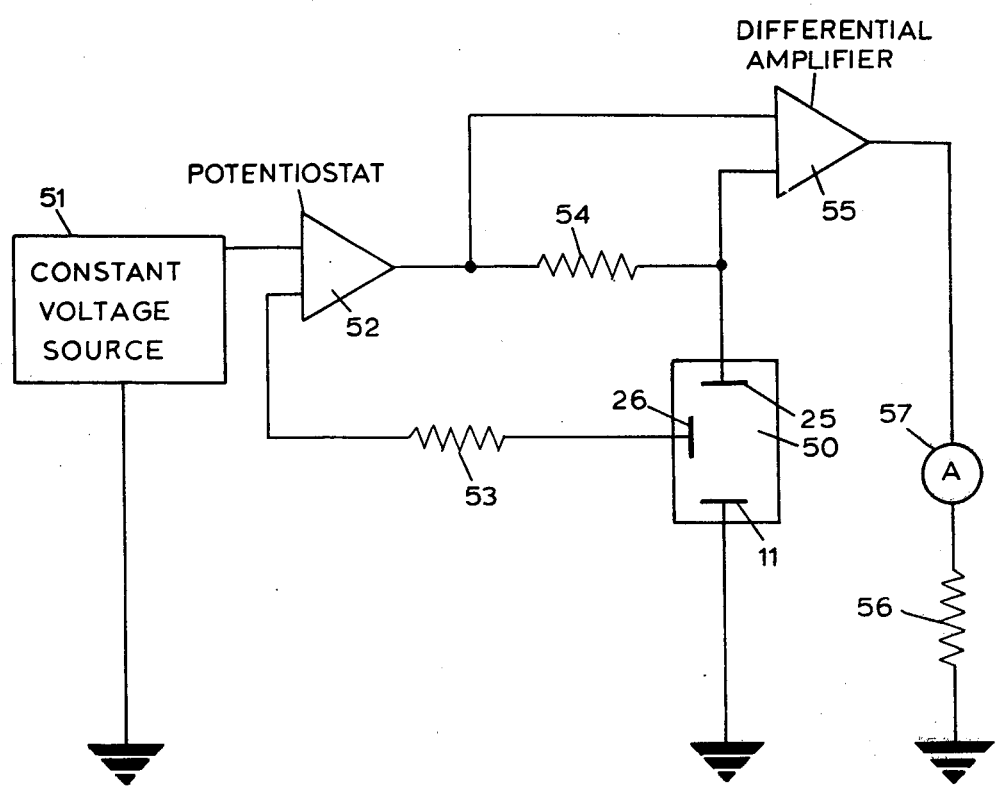
FIG. 2 is a simple circuit in which the sensor may be used.

Turning now to FIG. 2, in which the cell 50 is represented schematically, an earthed constant voltage source 51 provides one input to a potentiostat 52, the other input being from the reference electrode 26 of the cell through a constant resistance 53. The output of the potentiostat 52 is applied through a constant resistance 54 (equal in value to 53). By this means the potential difference between the reference electrode 26 and the oxygen diffusion electrode 11 is held constant. The two inputs of a differential amplifier circuit 55 which has a variable gain are taken from the ends of the resistance 54 and the output passes to earth through a resistance 56 and an ammeter 57 which is calibrated in oxygen content. When oxygen is present in the atmosphere, it is reduced at the oxygen diffusion electrode and a current flows in the cell 50. This generates a potential difference across the resistance 54 which is detected by the differential amplifier circuit 55 and read off on the ammeter 57. The characteristics of the differential amplifier 55 and the various resistances 53, 54 and 56 are chosen so that the current registered on the ammeter 57 is the current in the cell 50 due to the oxygen content of the atmosphere with which the cell is in contact.

It will be readily apparent to those skilled in the art that other circuits may be employed to detect the current output from the cell due to the presence of oxygen in the atmosphere.

The circuitry necessary to heat the sensor (heating coil 30 in FIG. 1 and/or heating coil (not shown) in the electrolyte itself), to monitor by means of the thermocouple 37 and maintain the temperature of the sensor substantially constant at a predetermined temperature is within the skill of the electronic art and is not illustrated.

The remaining figures are graphs which show the relationship of current output of the sensor to oxygen content under varying conditions.

Figure 3:
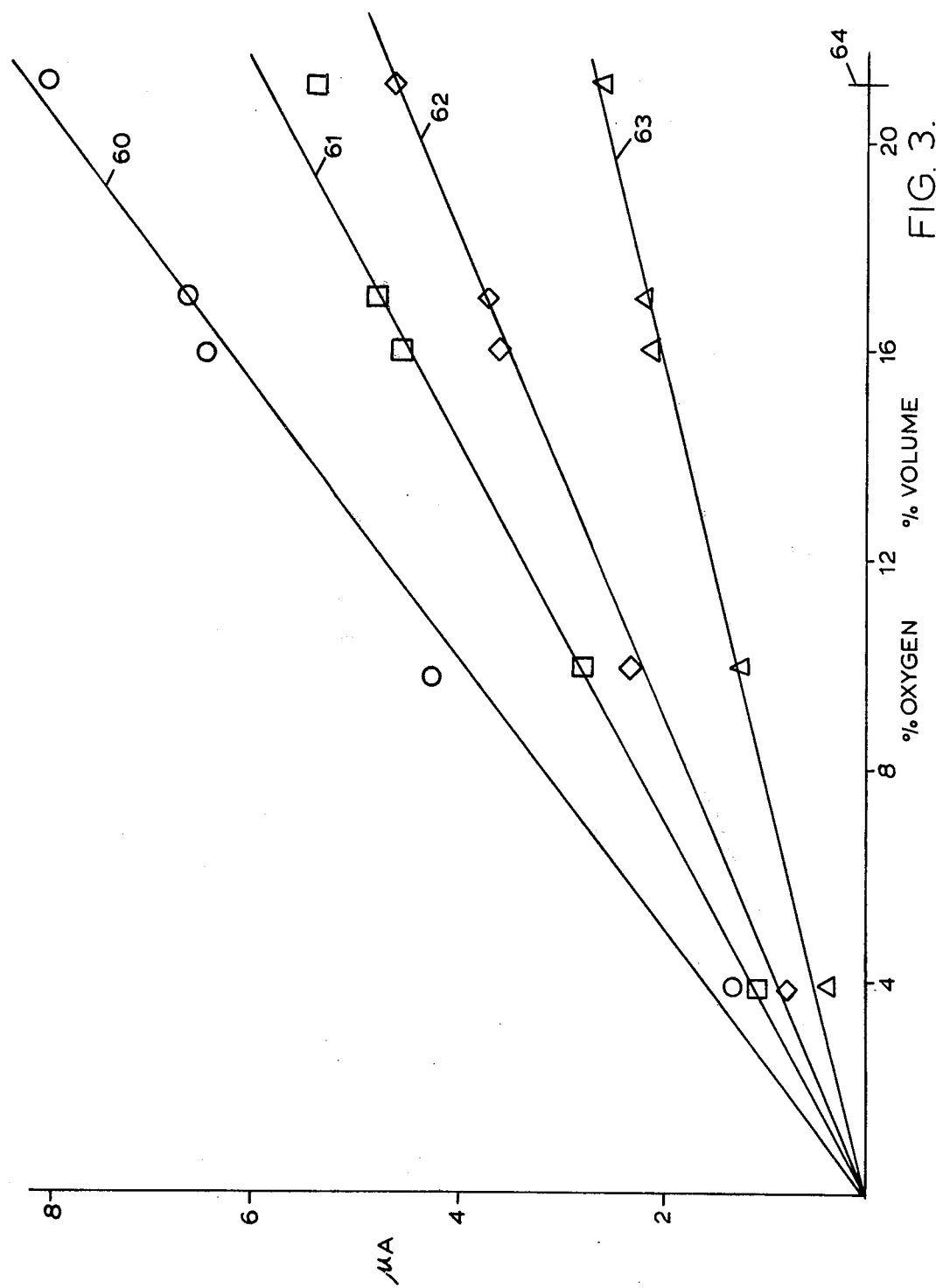
FIG. 3 shows the current output, against volume % of oxygen.

FIG. 3 shows the relationship current output of the sensor and oxygen content, in volumes %, at various pressures. The lines 60, 61, 62 and 63 refer respectively to atmospheric pressure, 0.75 atmospheres, 0.5 atmospheres, and 0.25 atmospheres. The point 64 refers to air.

Figure 4:
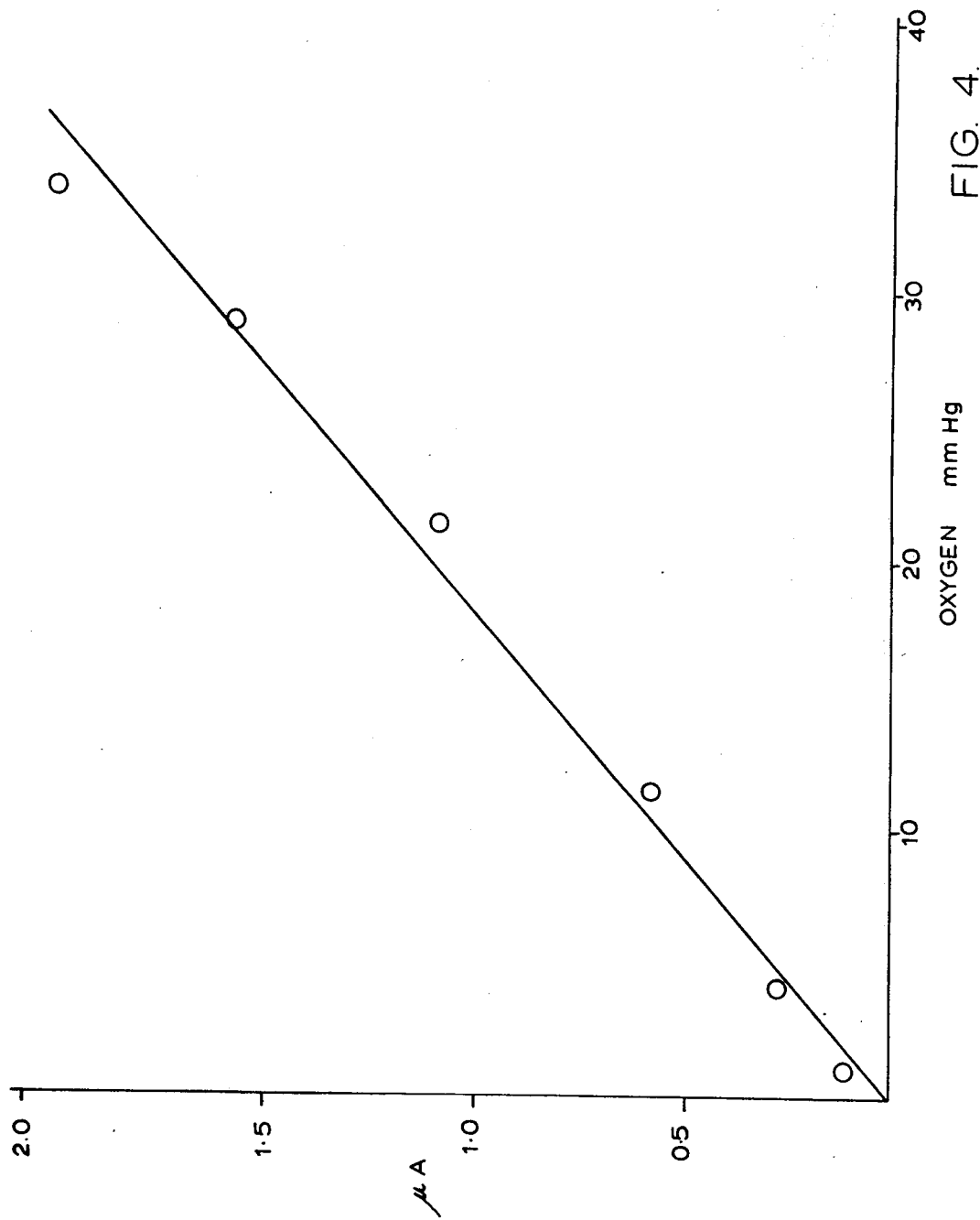
FIG. 4 shows the current output against oxygen content at low oxygen contents.

FIG. 4 shows the relationship at atmospheric pressure but at low oxygen contents, the oxygen content being indicated in mm Hg of oxygen.

Although the sensor is described herein used in the determination of oxygen in the atmosphere, it may also be employed to determine oxygen concentration in liquids, for example hydrocarbons and the like, with an appropriate additional scale on the meter. The only restrictions on the liquid which can be tested by the sensor herein described are that it should boil at a higher temperature than the operating temperature of the sensor and that it should not attack the polytetrafluoroethylene of the oxygen diffusion electrode.

We claim:

1. An oxygen sensor which comprises an electrochemical cell including
   (a) a gas diffusion electrode as the cathode, or working electrode,
   (b) a counter electrode as anode,
   (c) a reference electrode, and
   (d) a mass of salt which when molten constitutes an electrolyte in contact with said electrodes, the sensor also comprising
   (e) means for maintaining the working electrode (a) at a constant potential with reference to the reference electrode, and
   (f) means for determining the current flowing in the electrochemical cell due to reduction at the oxygen diffusion electrode (a) of oxygen present in the environment of the oxygen sensor, wherein the counter electrode (b) is a noble metal and the reference electrode (c) is a noble metal/noble metal oxide electrode.

2. An oxygen sensor as claimed in claim 1 and wherein the noble metal of the counter eletrode (b) and the reference electrode (c) is platinum.

3. An oxygen sensor as claimed in claim 2 and wherein the gas diffusion electrode (a) is a silver metallised polytetrafluoroethylene membrane.

4. An oxygen sensor as claimed in claim 3 and wherein the gas diffusion electrode (a) is a film of polytetrafluoroethylene 6 μm thick, one side of which has been covered by a coating of evaporated or sputtered gold followed by one of silver to ensure good adhesion between the silver and the polytetrafluoroethylene.

5. An oxygen sensor as claimed in claim 1 and wherein the reference electrode (c) is a platinum/platinum oxide electrode prepared by the steps of:
   (1) boiling a platinum wire in aqua regia to thoroughly clean it, and
   (2) immersing the cleaned wire in molten potassium nitrate at a temperature in excess of 400° C. for at least one hour while bubbles of gas evolve from around the wire.

6. An oxygen sensor as claimed in claim 1 and wherein the salt electrolyte (d) is an eutectic of sodium, potassium, and lithium nitrates.

7. An oxygen sensor as claimed in claim 1 and which includes a heating means and a thermostatic means arranged to cooperate so that the sensor may operate in an environment having an ambient temperture below the melting point of the salt electrolyte (d).

* * * * *